United States Patent
Bombarda et al.

(10) Patent No.: US 7,420,057 B2
(45) Date of Patent: Sep. 2, 2008

(54) STABLE POLYMORPH OF FLIBANSERIN

(75) Inventors: Carlo Bombarda, Chester, VA (US); Enrica Dubini, Milan (IT); Antoine Ezhaya, Milan (IT); Heinrich Schneider, deceased, late of Ingelheim (DE); by Margarete Schneider, legal representative, Ingelheim (DE)

(73) Assignee: Boehringer Ingelheim Pharma KG, Ingelheim (DE)

(*) Notice: Subject to any disclaimer, the term of this patent is extended or adjusted under 35 U.S.C. 154(b) by 0 days.

(21) Appl. No.: 11/546,304

(22) Filed: Oct. 12, 2006

(65) Prior Publication Data

US 2007/0032655 A1  Feb. 8, 2007

Related U.S. Application Data

(63) Continuation of application No. 10/210,474, filed on Aug. 1, 2002, now Pat. No. 7,183,410.

(60) Provisional application No. 60/329,435, filed on Oct. 15, 2001.

(30) Foreign Application Priority Data

Aug. 2, 2001 (EP) ................ 01118593
Dec. 19, 2001 (EP) ................ 01130180

(51) Int. Cl.
C07D 403/00 (2006.01)

(52) U.S. Cl. .............. 544/370; 544/366; 544/295; 514/254.06; 514/253

(58) Field of Classification Search ............ 514/254.06, 514/253; 544/370, 366, 295
See application file for complete search history.

(56) References Cited

U.S. PATENT DOCUMENTS

| | | | |
|---|---|---|---|
| 3,406,178 A | 10/1968 | Crocker et al. | |
| 3,472,854 A | 10/1969 | Archer | |
| 4,200,641 A | 4/1980 | Vandenberk et al. | |
| 4,737,500 A | 4/1988 | Sorg | |
| 4,792,452 A | 12/1988 | Howard et al. | |
| 4,797,399 A | 1/1989 | Ueda et al. | |
| 4,859,692 A | 8/1989 | Bernstein et al. | |
| 4,886,803 A | 12/1989 | Sueda et al. | |
| 4,940,793 A | 7/1990 | Botre et al. | |
| 4,954,503 A | 9/1990 | Strupczewski et al. | |
| 4,968,508 A | 11/1990 | Oren et al. | |
| 5,002,948 A | 3/1991 | Perregaard et al. | |
| 5,036,088 A | 7/1991 | Kitaura et al. | |
| 5,225,417 A | 7/1993 | Dappen et al. | |
| 5,405,642 A | 4/1995 | Gilis | |
| 5,434,156 A | 7/1995 | Bjoerk et al. | |
| 5,576,318 A | 11/1996 | Bietti et al. | |
| 5,591,743 A | 1/1997 | Patoiseau et al. | |
| 5,854,290 A | 12/1998 | Arnsten et al. | |
| 5,883,094 A | 3/1999 | Fliri et al. | |
| 5,977,106 A | 11/1999 | Patoiseau et al. | |
| 6,083,947 A | 7/2000 | Granger et al. | |
| 6,165,513 A | 12/2000 | Dansereau et al. | |
| 6,281,218 B1 * | 8/2001 | Cereda et al. ......... 514/254.06 |
| 6,284,757 B1 | 9/2001 | Sanner | |
| 6,426,087 B1 | 7/2002 | Saslawski | |
| 6,521,623 B1 | 2/2003 | Cereda et al. | |
| 6,586,435 B2 | 7/2003 | Cereda et al. | |
| 6,680,071 B1 | 1/2004 | Johnson et al. | |
| 7,151,103 B2 | 12/2006 | Borsini et al. | |
| 7,183,410 B2 | 2/2007 | Bombarda et al. | |
| 2003/0060475 A1 | 3/2003 | Borsini | |
| 2003/0083228 A1 | 5/2003 | Carpino et al. | |
| 2003/0119850 A1 | 6/2003 | Bombarda et al. | |
| 2004/0023948 A1 | 2/2004 | Green | |
| 2004/0048877 A1 | 3/2004 | Friedl et al. | |
| 2004/0116532 A1 | 6/2004 | Heacock et al. | |
| 2004/0147581 A1 | 7/2004 | Taylor | |
| 2004/0180904 A1 | 9/2004 | Beck | |
| 2004/0235861 A1 | 11/2004 | Borsini | |
| 2005/0004105 A1 | 1/2005 | Leahy et al. | |
| 2005/0037983 A1 | 2/2005 | Dinan et al. | |
| 2005/0065158 A1 | 3/2005 | Naylor et al. | |
| 2005/0159430 A1 | 7/2005 | Bombarda et al. | |
| 2005/0239798 A1 | 10/2005 | Pyke | |
| 2005/0245539 A1 | 11/2005 | Mendla et al. | |
| 2006/0014757 A1 | 1/2006 | Pyke | |
| 2006/0025420 A1 | 2/2006 | Brauns et al. | |
| 2006/0052391 A1 | 3/2006 | Dolsten | |
| 2006/0160822 A1 | 7/2006 | Borsini | |
| 2006/0199805 A1 | 9/2006 | Pyke et al. | |

(Continued)

FOREIGN PATENT DOCUMENTS

BE 904945 12/1986

(Continued)

OTHER PUBLICATIONS

U.S. Appl. No. 11/079,070, Bombarda et al.
U.S. Appl. No. 11/546,303, Bombarda et al.
U.S. Appl. No. 60/658,551, Pyke.
U.S. Appl. No. 60/658,566, Pyke.
U.S. Appl. No. 60/658,611, Pyke.
U.S. Appl. No. 60/734,405, Pyke et al.
Archer, T. "5HT, Pain and Anxiety." Behavioural Pharmacology of 5-HT (1989), pp. 299-300.
Awouters et al. "Oxatomide, a new orally active drug which inhibits both the release and the effects of allergic mediators." Chemical Abstracts, vol. 88, No. 15, 88:98788c (Apr. 10, 1978).
Basson et al. "Report of the International Consensus Development Conference on Female Sexual Dysfunction: Definitions and Classifications." The Journal of Urology, vol. 163 (Mar. 2000), pp. 888-893.
Beers et al., ed. The Merck Manual of Diagnosis and Therapy, 17th ed. (1999), pp. 1595-1598.

(Continued)

*Primary Examiner*—Yvonne Eyler
*Assistant Examiner*—Chukwuma O Nwaonicha
(74) *Attorney, Agent, or Firm*—Boehringer Ingelheim Corp

(57) ABSTRACT

The invention relates to the polymorph A of flibanserin, to a technical process for the preparation thereof, as well as to the use thereof for preparing medicaments.

16 Claims, 1 Drawing Sheet

U.S. PATENT DOCUMENTS

| | | | |
|---|---|---|---|
| 2006/0204486 A1 | 9/2006 | Pyke et al. |
| 2006/0211685 A1 | 9/2006 | Pyke et al. |
| 2006/0252773 A1 | 11/2006 | Ceci |
| 2006/0258640 A1 | 11/2006 | Ceci et al. |
| 2006/0264511 A1 | 11/2006 | Pyke |
| 2006/0264512 A1 | 11/2006 | Pyke |
| 2007/0032654 A1 | 2/2007 | Bombarda |
| 2007/0072872 A1 | 3/2007 | Borsini |
| 2007/0105869 A1 | 5/2007 | Pollentier et al. |
| 2007/0123540 A1 | 5/2007 | Ceci |
| 2007/0196473 A1 | 8/2007 | Friedl et al. |
| 2008/0038346 A1 | 2/2008 | Eisenreich et al. |
| 2008/0038347 A1 | 2/2008 | Eisenreich et al. |
| 2008/0069873 A1 | 3/2008 | Pearnchob et al. |

FOREIGN PATENT DOCUMENTS

| | | |
|---|---|---|
| CA | 2455628 | 2/2003 |
| DE | 3620643 | 1/1987 |
| DE | 10138273 | 2/2003 |
| EP | 0200322 | 11/1986 |
| EP | 376607 | 4/1990 |
| EP | 497985 | 12/1992 |
| EP | 0 526 434 A1 * | 2/1993 |
| EP | 0526434 | 2/1993 |
| EP | 0705832 | 4/1996 |
| EP | 0816356 | 1/1998 |
| EP | 0982030 | 3/2000 |
| EP | 1256343 | 11/2002 |
| EP | 1285658 | 2/2003 |
| EP | 1518858 | 3/2005 |
| EP | 1674102 | 6/2006 |
| GB | 2023594 | 1/1980 |
| IE | 1992/1340 | 10/1992 |
| JP | H8-143476 | 6/1996 |
| WO | WO 92/03167 | 3/1992 |
| WO | WO 92/19606 | 11/1992 |
| WO | WO 93/03016 | 2/1993 |
| WO | WO 95/01965 | 1/1995 |
| WO | WO 95/34555 | 12/1995 |
| WO | WO 96/05834 | 2/1996 |
| WO | WO 96/16949 | 6/1996 |
| WO | WO 98/33784 | 8/1998 |
| WO | WO 98/42344 | 10/1998 |
| WO | WO 99/19302 | 4/1999 |
| WO | WO 00/28993 | 5/2000 |
| WO | WO 00/64441 | 11/2000 |
| WO | WO 01/12170 | 2/2001 |
| WO | WO 01/21593 | 3/2001 |
| WO | WO 02/24662 | 3/2002 |
| WO | WO 02/079143 | 10/2002 |
| WO | WO 03/011396 | 2/2003 |
| WO | WO 03/013539 | 2/2003 |
| WO | WO 03/014079 | 2/2003 |
| WO | WO 03/035072 | 5/2003 |
| WO | WO 03/097058 | 11/2003 |
| WO | WO 2004/041259 | 5/2004 |
| WO | WO 2004/045509 | 6/2004 |
| WO | WO 2004/069339 | 8/2004 |
| WO | WO 2005/007166 | 1/2005 |
| WO | WO 2005/102343 | 3/2005 |
| WO | WO 2005/044238 | 5/2005 |
| WO | WO 2005/087207 | 9/2005 |
| WO | WO 2005/102342 | 11/2005 |
| WO | WO 2006/010574 | 2/2006 |
| WO | WO 2006/019715 | 2/2006 |
| WO | WO 2006/096435 | 9/2006 |
| WO | WO 2006/125041 | 11/2006 |
| WO | WO 2007/014929 | 2/2007 |
| WO | WO 2007/048803 | 3/2007 |

OTHER PUBLICATIONS

Bernstein, J. et al. "Concomitant Polymorphs." Angewandte Chemise, Int. Ed. (1999), pp. 3441-3461.

Bevan et al. "5-HT and Sexual Behaviour." Behavioural Pharmacology of 5-HT, pp. 33-34, 87-88 (1989).

Borsini et al. "Behavioral Effects of Flibanserin (BIMT-17)," Pharmacology, Biochemistry and Behavior, vol. 64, issue 1 (Sep. 1999), see abstract.

Borsini et al., Flibanserin, Drugs of the Future, 23(1):9-16 (1998).

Borsini, F. et al. "BIMT-17, a 5HT-2A Receptor Antagonist and 5HT-1A Receptor Full Agonist in Rat Cerebral Cortex," Naunyn-Schmiedeberg's Archives of Pharm., 352(3):276-82 (1995).

Chalmers et al. "Corticotrophin-releasing Factor Receptors: from Molecular Biology to Drug Design." TiPS vol. 17 (Apr. 1996), pp. 166-172.

Cloninger, C. R. "A Systematic Method for Clinical Description and Classification of Personality Variants." Arch. Gen. Psychiatry, vol. 44 (Jun. 1987), pp. 573-588.

Collino, F. et al. Chemical Abstract: Database Accession No. 98:16650-XP 002197885: Mannich bases of benzimidazoles, benzotriazoles and other analogous compounds, with pharmacological activity.

Cools, A. R. "Depression and Psychosis," Behavioural Pharmacology of 5-HT (1989), pp. 153-155.

Crook, T. & Lakin, M. "Effects of Ondansetron in Age-associated Memory Impairment." The role of ondansetron, a novel 5-HT3 antagonist, in the treatment of psychiatric disorders, 5th World Congress of Biochemical Psychiatry, pp. 21-23 (1991).

Cyr et al. "Nefazodone: Its Place among Antidepressants." Annals of Pharmacotherapy 30(9): 1006-12 (1996).

Damour et al. "Preparation and formulation of 1-[(4-phenyl=piperazino)alkyl]benzimidazolin-2-ones and analogs as serotonin S2 antagonists." Chemical Abstracts, vol. 118, No. 13, 118:124537e (Mar. 29, 1993).

Darlington, C. "Flibanserin." Current Opinion in CPNS Investigational Drugs, 1(4): 510-13 (1999).

De Angelis. "5-HT2A antagonists in psychiatric disorders." Current Opinion in Investigational Drugs, vol. 3, N.R. 1, pp. 106-112 (2002).

De Vry, J. "5-HT1A receptors in psychopathology and the mechanism of action of clinically effective therapeutic agents," Drug News and Perspectives 9(5): 270-80 (1996).

Dimmock, P. et al. "Efficacy of Selective Serotonin-Reuptake Inhibitors in Premenstrual Syndome: A Systematic Review." The Lancet, vol. 356, No. 9236 (Sep. 30, 2000), pp. 1131-1136.

Fourcroy, Jean L. "Female Sexual Dysfunction: Potential for Pharmacotherapy." Drugs, vol. 63, No. 14 (2003), pp. 1445-1457.

Frampton et al. "Pentoxifylline (oxpentifylline): A Review of its Therapeutic Efficacy in the Management of Peripheral Vascular and Cerebrovascular Disorders." Drug Evaluation, Drugs and Aging 7(6), pp. 480-503 (1995).

Geyer, M. "5-HT2 Antagonists Increase Tactile Startle Habituation in an Animal Model of Habituation Deficit in Schizophrenia." Behavioural Pharmacology of 5-HT, pp. 243-246 (1989).

Giron, D. "Thermal Analysis and Calorimetric Methods in the Characterization of Polymorphs and Solvates." Thermochimica ACTA, Elsevier Science, 248 (1995), pp. 1-59.

Goa et al. "Buspirone: A preliminary review of its pharmacological properties and therapeutic efficacy as an anxiolytic." Drugs 32:114-29 (1986).

Gould. "Salt Selection for Basic Drugs." International Journal of Pharmaceutics vol. 33, Issues 1-3 (Nov. 1986), pp. 201-217.

Greene, T. "Protective Groups in Organic Synthesis." Havard University (Wiley-Interscience Publication, 1981), pp. 10-17.

Hansenne, M. et al. "Harm avoidance dimension of the tridimensional personality questionnaire and serotonin-1A activity in depressed patients." Biol. Psychiatry 42: 959-61 (1997).

Invernizzi et al. "Flibanserin, a Potential Antidepressant Drug, Lowers 5-HT and Raises Dopamine and Noradrenaline in the Rat Prefrontal Cortex Dialysate: Role of 5-HT1A Receptors." British Journal of Pharmacology, vol. 139 (Jun. 2003), pp. 1281-1288.

Lammers G.J. et al. "Ritanserin, a 5-HT$_2$ receptor blocker, as add-on treatment in narcolepsy." Sleep 14(2): 130-32 (1991).
Leonard, B. E. "Sub-types of Serotonin Receptors: Biochemical Changes and Pharmacological Consequences." International Clinical Psychopharmacology 7: 13-21 (1992).
Lyrer. "Neue Ansatze in der Akutbehandlung des zerebrovaskularen Insultes." Schweiz. Med. Wochenschr., vol. 124, No. 45 (1994), pp. 2005-2012.
McCall, R.B. et al. "Role of serotonin$_{1A}$ and serotonin$_2$ receptors in the central regulation of the cardiovascular system." Pharmacological Reviews 46(3): 231-43 (1994).
Petkov, V.D. et al. "Participation of different 5-HT receptors in the memory process in rats and its modulation by the serotonin depletor p-chlorophenylalanine." Acta Neurobiol. Exp. 55: 243-52 (1995).
Podhorna et al. "Flibanserin has Anxiolytic Effects without Locomotor Side Effects in the Infant Rat Uultrasonic Vocalization Model of Anxiety." British J. of Pharm., vol. 130, No. 4 (2000), pp. 739-746.
Reikkinen et al. "The Effects of Increased Serotonergic and Decreased Cholinergic Activities on Spatial Navigation Performance in Rats." Pharmacology Biochemistry & Behavior, vol. 39 (1991), pp. 25-29.
Reuter, L. E. et al. "Electrophysiological Examination of the Effects of Sustained Flibanserin Administration on Serotonin Receptors in Rat Brain." British J. of Pharm., vol. 126, No. 3 (1999), pp. 627-638.
Risch, S. Craig et al. "Neurochemical alterations of serotonergic neuronal systems in depression." J. Clin. Psychiatry 53(10) Suppl: 3-7 (1992).
Robinson, DS. "Serotonin receptor subtypes and affective disorders." Clinical Neuropharmacology 16(S3): S1-S5 (1993).
Steiner, M. "Recognition of Premenstrual Dysphoris Disorder and its Treatment." The Lancet, vol. 356, No. 9236 (Sep. 30, 2000), pp. 1126-1127.
Vaudenberk et al. "Piperazine and Piperidine Derivatives." Chemical Abstracts, vol. 88, No. 5, 88:50920n (Jan. 30, 1978).
Zajecka et al. "Sexual Function and Satisfaction in the Treatment of Chronic Major Depression with Nefazodone, Psychotherapy, and their Combination." Journal of Clinical Psychiatry, 63(8): 709-16 (Aug. 2002).
U.S. Appl. No. 10/272,603, filed Dec. 19, 2006, Borsini et al.
U.S. Appl. No. 11/364,153, filed Sep. 21, 2006, Pyke et al.
U.S. Appl. No. 11/079,070, filed Jul. 21, 2005, Bombarda et al.
U.S. Appl. No. 11/524,268, filed Mar. 29, 2007, Borsini et al.
U.S. Appl. No. 11/550,869, filed May 31, 2007, Ceci.
U.S. Appl. No. 11/837,957, Eisenreich et al.
U.S. Appl. No. 11/837,959, Eisenreich et al.
U.S. Appl. No. 11/837,962, Pearnchob et al.
U.S. Appl. No. 60/348,911, Borsini et al.
Aizenberg, et al., "Cyproheptadine Treatment of Sexual Dysfunction Induced by Serotonin Reuptake Inhibitors," Clinical Nueropharmacology, vol. 18, No. 4, pp. 320-324 (1995).
Baxter, G., "5-HT2 Receptor Subtypes: a family re-united?", Trends in Pharmacological Sciences, Elsevier, Haywarth, GB, vol. 16, No. 3, Mar. 1995, pp. 105-110.
Borsini et al., "Behavioral Effects of Flibanserin (BIMT 17)," Sep. 1999, Pharmacology Biochemistry and Behavior, vol. 64, Issue 1, pp. 137-146.
Borsini, et al., "Lack of interaction between flibanserin and antidepressants in inducing serotonergic syndrome in rats," International Journal of Neuropsychopharmacology 4(1): 9-15 (2001).
Borsini, et al., "Mechanism of action of flibanserin in the learned helplessness paradigm in rats," European Journal of Pharmacology 433: 81-89 (2001).
Borsini, et al., "Pharmacology of Flibanserin" CNS Drug Reviews 2002; vol. 8, No. 2, pp. 117-142.
Brambilla, et al., "Effect of flibanserin (BIMT 17), fluoxetine, 8-)H-DPAT and buspirone on serotonin synthesis in rat brain," European Neuropsychopharmacology 10(1): 63-67 (1999).
Carey, John, "Viagra for Women?" BusinessWeek.com (Dec. 28, 2006).
Cesana, et al., "The effect of BIMT 17, a new potential antidepressant, in the forced swimming test in mice," Behavioural Pharmacology 6: 688-94 (1995).

Cremers, et al., "Non Erectile Dysfunction Application of Sildenafil", Herz, vol. 28, No. 4, pp. 325-333, 2003.
Damir et al., "Hemodynamic effects of pharmacological block during acute overload of the heart" Database accession # 1978:591197 XP-002436715.
Gonzales, S., "Natural Compound May Offer New Treatment for Chronic Pain," NDA Notes, vol. 16, No. 3 (2001).
Kleven, M., "Modification of behavioral effects of 8-hydroxy-2-(di-n-propylamino) tetralin following chronic ethanol consumption in the rat: evidence for the involvement of 5-HT1A receptors in ethanol dependence.", European Journal of Pharmacology, 1995, vol. 281, No. 3, pp. 219-228.
Koba, "Involvement of peripheral 5-HT2A receptor activation in pain behaviour evoked by formalin paw injection in the rat," Kyushu Shika Gakkai Zaahi 53(1): 253-60 (1999).
Marazziti, et al., "Region-dependent effects of flibanserin and buspirone on adenylyl cyclase activity in the human brain," Int'l Journal of Neuropsychopharmacology 5(2): 131-40 (Jun. 2002).
Martindale, "Anxiolytic Sedatives Hypnotics and Antipsychotics," The Complete Drug Reference, p. 635 (1999).
"Merck Manual of diagnosis and therapy", Merck Research Laboratories, USA 1999, p. 1410, col. 1—p. 1413, col. 2, paragraph 1; p. 1412, tables 173-2 XP-002439435.
Meston, C., et al., "Psychoactive Drugs and Human Sexual Behavior: The Role of Serotonergic Activity," J. of Psychoactive Drugs vol. 24(1): 1-40 (1992).
Miranda, H., et al., "Dexketoprofen-induced Antinociception in Animal Models of Acute Pain: Synergy With Morphine and Paracetamol," Nueropharmacology 52 (2007) 291-296.
Moynihan, R., "The making of disease: female sexual dysfunction" British Medical Journal, 2003. vol. 326, pp. 45-47.
Nadeson, et al., "Antinoceptive role of 5-HT1A receptors in rat spinal cord," British Journal of Anaesthesia 88(5): 679-84 (2002).
Okamoto, K., et al., "5-HT2A receptor Subtype in the Peripheral Branck of Sensory Fibers is Involved in the Potentiation of Inflammatory Pain in Rats," Pain 99 (2002) 133-143.
Phillips, R., Jr., et al., "Depression and Sexual Desire," American Family Physician, vol. 62 No. 4 (2000).
Rosland, J., et al., "The Formalin Test in Mice: Effect of Formalin Concentration," Pain 42 (1990) 235-242.
Shipton, B. et al., "Valvular heart disease: review and update," American Family PhysicianJun. 1, 2001, vol. 63 # 11, pp. 2201-2208.
Sietsema, D. et al., "From Taboo to Treatment?" Good Clinical Practice Journal, Jan. 2005, vol. 12, # 1, pp. 23-27.
Walsh, K. et al., "Sexual dysfunction in the older women and overview of the current understanding and management" Drugs and Aging, 2004, vol. 21, # 10 pp. 655-675.
"Types of Back Pain: Acute Pain, Chronic Pain, and Neuropathic Pain," Spine-health.com, www.spine-health.com/topics/cd/chronicpain02.html, (Oct. 2, 2007).
Office Action dated Jan. 5, 2007 in U.S. Appl. No. 11/546,303.
Response dated Jul. 5, 2007 in U.S. Appl. No. 11/546,303.
Office Action dated Sep. 14, 2007 in U.S. Appl. No. 11/546,303.
Interview Summary dated Nov. 19, 2007 in U.S. Appl. No. 11/546,303.
Office action dated Jul. 26, 2004 in U.S. Appl. No. 10/210,474.
Response and declaration dated Jan. 24, 2005 in U.S. Appl. No. 10/210,474.
Reply with Amendment in response to telephone interview of Mar. 8, 2005 in U.S. Appl. No. 10/210,474.
Office Action dated Mar. 16, 2005 in U.S. Appl. No. 10/210,474.
Office Communication dated Apr. 12, 2005 in U.S. Appl. No. 10/210,474.
Amendment dated Jul. 8, 2005 in U.S. Appl. No. 10/210,474.
Office Action dated Oct. 5, 2005 in U.S. Appl. No. 10/210,474.
Response dated Dec. 15, 2005 in U.S. Appl. No. 10/210,474.
Applicant Initiated Interview Request Form dated Jan. 13, 2006 in U.S. Appl. No. 10/210,474.
Backhauβ, et al., "A Mouse Model of Focal Cerebral Ischemia for Screening Neuroprotective Drug Effects," Journal of Pharmacological Methods 27, 27-32 (1992).
Borsini, et al., "BIMT 17: a putative antidepressant with a fast onset of action?" Psychopharmacology (1977) 134:378-386.

Fujikura, et al., "Effects of naftidrofurly oxalate, a 5-$HT_2$ antagonist, on neuronal damage and local cerebral blood flow following transient cerebral ischemia in gerbils." Brain Research 636 (1994) 103-106.

Prehn, et al., "Neuroprotective properties of 5-$HT_{1A}$ receptor agonists in rodent models of focal and global cerebral ischemia," European Journal of Pharmacology 203 (1991) 213-222.

Prehn, et al., "Effects of serotonergic drugs in experimental brain ischemia: evidence for a protective role of serotonin in cerebral ischemia." Brain Research 630 (1993) 10-20.

Shibata, et al., "Ischemia-induced impairment of 2-deoxyglucose uptake and CA1 field potentials in rat hippocampal slices: protection by 5-$HT_{1A}$ receptor agonists and 5-$HT_2$ receptor antagonists." European Journal of Pharmacology, 229 (1992) 21-29.

New Collegiate Dictionary 1981, p. 311 (definition of term "diagnosis").

Frampton, et al., "Pentoxifylline (oxpentifylline): A Review of its Therapeutic Efficacy in the Management of Peripheral Vascular and Cerebrovascular Disorders," Drug Evaluation, Drugs and Aging 7(6). pp. 480-503 (1995).

U.S. Appl. No. 11/956,949, filed Dec. 14, 2007, D. Lewis-D'Agostino et al.

U.S. Appl. No. 11/960,957, filed Dec. 20, 2007, Mendla et al.

U.S. Appl. No. 11/940,655, filed Nov. 15, 2007, Dolsten.

U.S. Appl. No. 11/997,567, filed Feb. 1, 2008, Ceci.

ISR PCT/EP 02/08466—WO 03/014079, dated Nov. 21, 2002.

\* cited by examiner

STABLE POLYMORPH OF FLIBANSERIN

RELATED APPLICATIONS

Benefit of U.S. application Ser. No. 11/546,304 filed Oct. 12, 2006, which is a continuation of U.S. application Ser. No. 10/210,474 filed Aug. 1, 2002, now U.S. Pat. No. 7,183,410, which is a non-provisional of U.S. Provisional Application Ser. No. 60/329,435, filed on Oct. 15, 2001, which is a provisional national filing of EP 01 118 593.1 filed Aug. 2, 2001 and EP 01 130 180.1 filed Dec. 19, 2001, is hereby claimed, and said applications are herein incorporated by reference in their entirety.

FIELD OF THE INVENTION

The invention relates to the polymorph A of flibanserin, to a technical process for the preparation thereof, as well as to the use thereof for preparing medicaments.

BACKGROUND OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure:

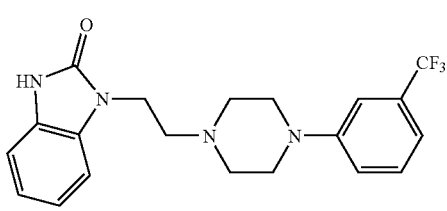

1xHCl

Flibanserin shows affinity for the 5-HT$_{1A}$ and 5-HT$_2$-receptor. It is therefore a promising therapeutic agent for the treatment of a variety of diseases, for instance depression, schizophrenia, Parkinson, anxiety, sleep disturbances, sexual and mental disorders and age associated memory impairment.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is absolutely essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is absolutely essential that the active substance should be highly stable throughout the grinding process. Only if the active substance is sufficiently stable during the grinding process is it possible to produce a homogeneous pharmaceutical formulation which always contains the specified amount of active substance in reproducible manner.

Another problem which may arise in the grinding process for preparing the desired pharmaceutical formulation is the input of energy caused by this process and the stress on the surface of the crystals. This may in certain circumstances lead to polymorphous changes, to a change in the amorphous configuration or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound flibanserin which meets the stringent requirements imposed on pharmaceutically active substances as mentioned above.

DETAILED DESCRIPTION OF THE INVENTION

Figure 1:
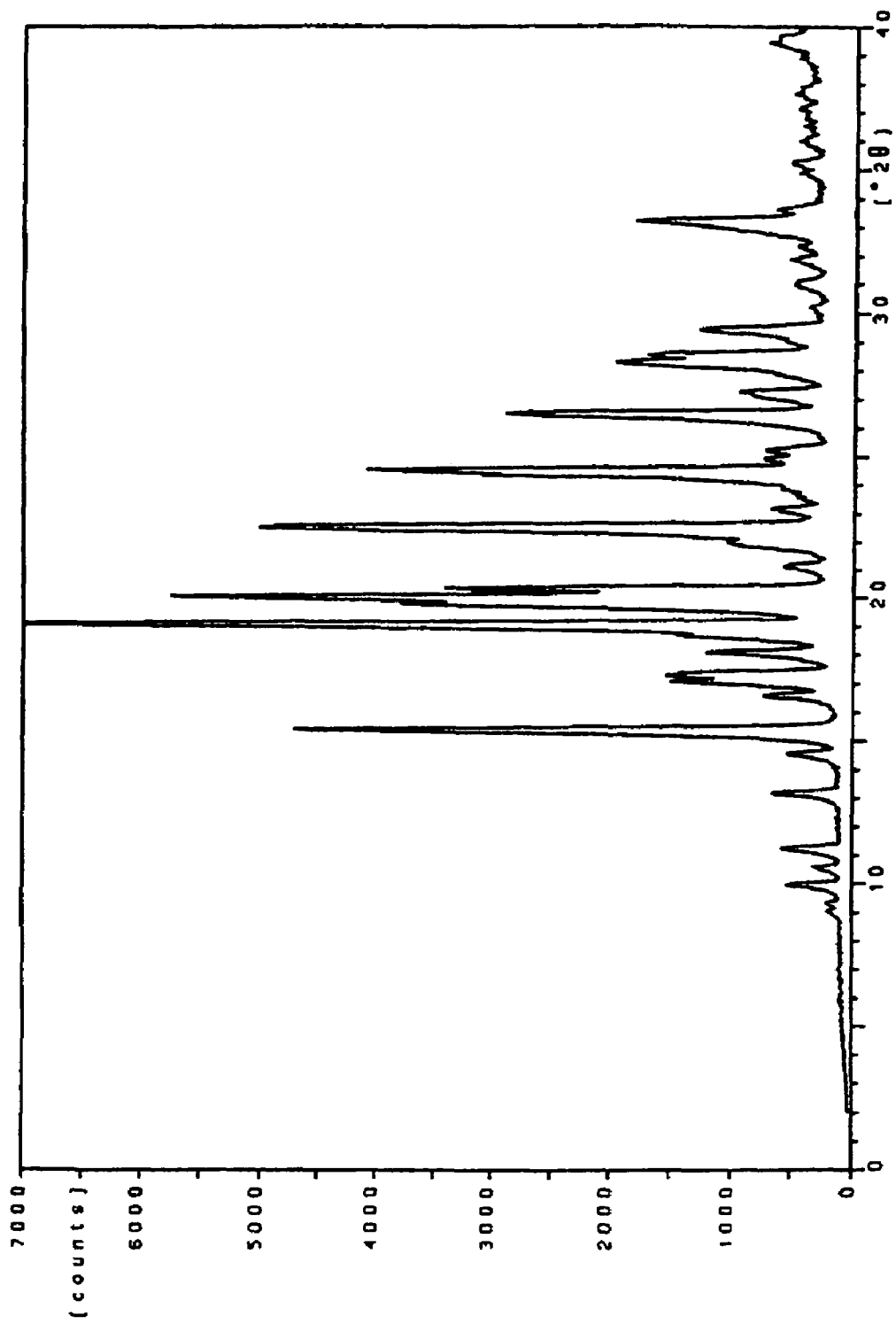
FIG. 1 shows the X-ray powder diffraction pattern of polymorph A of flibanserin.

Surprisingly, it has been found that the free base of flibanserin in a specific polymorphic form fulfils the requirements mentioned hereinbefore.

Moreover it has been found that, depending on the choice of conditions which can be applied during the synthesis of flibanserin the free base occurs in different crystalline modifications, polymorphs A and B.

It has been found that these different modifications can be deliberately produced by a suitable choice of the process conditions used in the manufacturing process.

Surprisingly, it has been found that polymorph A, which can be obtained in crystalline form by choosing specific reaction conditions, meets the stringent requirements mentioned above and thus solves the problem on which the present invention is based. Accordingly the present invention relates to polymorph A of flibanserin.

Polymorph A of flibanserin is characterised by a melting point of about 161° C. (determined via DSC; heating rate 10 K/min). 161° C. as determined using DSC.

Polymorph B, the less stable modification of flibanserin displays a melting point of about 120° C. (determined via DSC; heating rate 10 K/min). Whereas polymorph B shows little stability under the effects of for instance mechanical stress produced by grinding, polymorph A turned out to fulfil the aforementioned stability requirements.

According to another aspect, the present invention relates to a process for the manufacture of polymorph A of flibanserin in technical scale. The process according to the invention is illustrated in diagram 1.

Diagram 1:

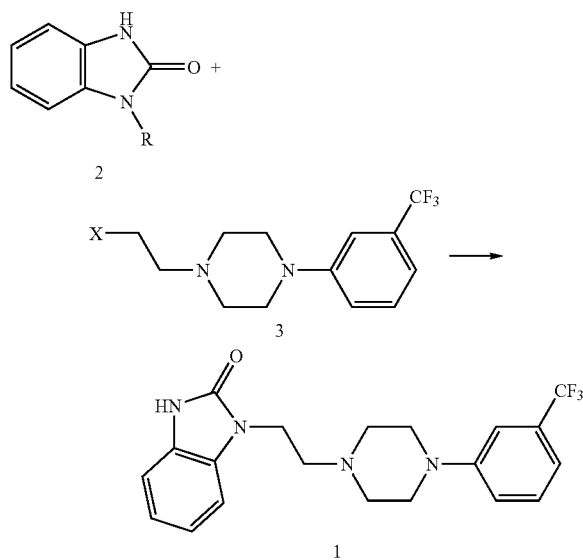

The benzimidazolone 2 is reacted with the piperazine-derivative 3 under basic reaction conditions in a suitable solvent to lead to 1. In 2 the group R denotes an amino protecting group. The protecting group used may be any of the groups commonly used to protect the amino function. Examples include groups selected from alkyl, substituted alkyl, heterosubstituted alkyl, unsaturated alkyl, alkyl substituted heteroatoms, substituted or unsubstituted phenyl, substituted or unsubstituted benzyl, alkyloxycarbonyl groups and aryloxycarbonyl groups. Preferred protecting groups are selected from butyl, 1,1-diphenylmethyl, methoxymethyl, benzyloxymethyl, trichloroethoxymethyl, pyrrolidinomethyl, cyanomethyl, pivaloyloxymethyl, allyl, 2-propenyl, t-butyldimethylsilyl, methoxy, thiomethyl, 4-methoxyphenyl, benzyl, 4-methoxybenzyl, 2,4-dimethoxybenzyl, 2-nitrobenzyl, t-butoxycarbonyl, benzyloxycarbonyl, phenoxy carbonyl, 4-chloro-phenoxycarbonyl, 4-nitro-phenoxycarbonyl, methoxycarbonyl and ethoxycarbonyl. Among them the preferred protecting groups are selected from t-butoxycarbonyl, ethoxycarbonyl, methoxycarbonyl, benzyloxycarbonyl, phenoxycarbonyl and 2-propenyl, the latter being most preferred. X in 3 represents a leaving group selected from chlorine, bromine, iodine, methanesulphonate, trifluoromethanesulphonate or para-toluenesulphonate. Preferably X denotes chlorine, bromine or iodine, chlorine being most preferred. Suitable solvents are selected from water, alcohols and mixtures of water with alcohols, polar aprotic solvents and mixtures thereof with water. Preferred solvents are selected from the group consisting of dimethylformamid, dimethylsulfoxid, acetonitrile, tetrahydrofurane, dioxane, methanol, ethanol isopropanaol and mixtures of one or several of the aforementioned solvents with water. Preferred solvents are those being readily miscible with water. Preferably, a mixture of water with one of the alcohols methanol, ethanol or isopropanol is used as the solvent. In a preferred embodiment a mixture of water and isopropanol is used as the solvent. The base used may be an alkali metal- or alkaline earth metal carbonate of lithium, sodium, potassium, calcium such as sodium carbonate, lithium carbonate, potassium carbonate, calcium carbonate and preferably potassium carbonate. It is also possible to use the hydrogen carbonates of lithium, sodium and potassium. Preferably, the alkali metal- or alkaline earth metal hydroxides of lithium, sodium, potassium, magnesium, calcium, but preferably sodium hydroxide, potassium hydroxide, lithium hydroxide and calcium hydroxide in alcohols or water may also be used. Most preferred base is sodium hydroxide. The base is preferably added in form of its aqueous solution, preferably in form of concentrated aqueous solutions, for example in concentrations between 30-50% weight/volume. In a preferred embodiment aqueous sodium hydroxide solution in a concentration of about 45% weight/volume is used.

The compounds 2 and 3 are introduced into the reaction in a molar ratio of between 1:1 to 1:2, preferably in a molar ratio of between 1:1.1 to 1:1.5.

As mentioned hereinbefore a mixture of water and isopropanol is used as a preferred solvent mixture for the conduction of the process according to the invention. In this solvent mixture the weight-ratio of water to isopropanol in the preferred solvent mixture is between 10:1 and 1:1, more preferred between 8:1 and 3:1, particular preferred between 7:1 and 5:1. Per mol of compound 2 about 2-10 kg, preferably 3-8 kg, more preferred 4-7 kg of the aforementioned solvent mixture are used. In a preferred embodiment the reaction is conducted using aqueous sodium hydroxide solution in a concentration of about 45% weight/volume as the base. Per mol of 2 about 0.1-1.5 kg, preferably 0.2-1.0 kg, particularly preferred 0.3-0.6 kg of the aforementioned sodium hydroxide solution are used. The reaction mixture containing 2, 3 and the base in the aforementioned suitable solvent is preferably heated to at least 50° C. In a preferred embodiment the reaction temperature is in a range of between 60° C. to the boiling point of the solvent. Particularly preferred is a temperature between 70-90° C. The reaction mixture is heated at the aforementioned temperature for about 10 minutes to about 12 hours, preferably for about 15 minutes to about 6 hours, more preferably for about 30 minutes to about 3 hours. The reaction mixture is preferably heated at the aforementioned temperature for about 45 to 60 minutes.

Subsequently the protective group R is cleaved. The cleaving conditions depend on the choice of group R. If R denotes for instance benzyl, cleavage is conducted via hydrogenation in acetic acid in the presence of an appropriate catalyst (e.g. Pd on charcoal) or it can be cleaved in aqueous HBr. In case R is methoxycarbonyl, ethoxycarbonyl, phenoxy carbonyl, 4-nitrophenoxycarbonyl it can be cleaved for example by using aqueous alkaline solutions such as NaOH (aq) or KOH (aq). In case R is t-butoxycarbonyl it can be cleaved for instance in aqueous HCl or HBr. In case R denotes 2-propenyl, the particularly preferred protective group according to the invention, cleavage of R is effected via acidic reaction conditions. In a particularly preferred process according to the invention the 2-propenyl group is cleaved by using a strong mineral acid, preferably an acid selected from the group consisting of hydrobromic acid, hydrochloric acid and sulfuric acid, more preferably hydrochloric acid. Hydrochloric acid can be added in gaseous form or in form of its aqueous solutions, the addition of aqueous solutions being preferred.

Particularly preferred is the addition of hydrochloric acid in form of its concentrated solution (about 36% weight/volume). Per mol 2 at least one mol of hydrochloric acid is to be added. Preferably the amount of added concentrated hydrochloric acid (36% weight/volume) per mol 2 is between 50-500 g, more preferred between 80-250 g. Particularly preferred about 120-160 g of concentrated (36% w/v) aqueous hydrochloric acid are added per mol 2 used. Additional water can be optionally added. At a temperature of about 70-90° C. about 30-70%, preferably about 35-60% of the solvent is removed via distillation. At a temperature of about 60-80° C. the pH of the remaining residue is adjusted to about 5-9, preferably to about 6-8 by addition of aqueous sodium hydroxide (45% w/v). At a temperature of about 40-55° C. the pH is adjusted to about 8-9 by addition of aqueous sodium hydroxide (45% w/v). Subsequently the mixture is cooled to about 20-40° C., preferably about 30-35° C. and centrifuged. The residue thus obtained is washed with about 100 to 750 ml water per mol introduced 2, preferably with about 200 to 500, particularly preferred with about 300 to 400 ml water per mol introduced 2 and isopropanol (about 50 to 250 g per mol 2, preferably about 100 to 200 g per mol 2) and then with water until chlorides elimination. Optionally the product thus obtained can be subjected to another purification step. Preferably, said purification is conducted via crystallization of 1 from for instance acetone.

One aspect of the present invention relates to flibanserin polymorph A obtainable via the method described above.

The following example of synthesis serves to illustrate a method of preparing polymorph A of flibanserin. It is to be regarded only as a possible method described by way of example, without restricting the invention to its contents.

EXAMPLE 375 kg of 1-[(3-trifluoromethyl)phenyl]-4-(2-cloroethyl) piperazin are charged in a reactor with 2500 kg of water and 200 kg of aqueous Sodium Hydroxide 45%. Under stirring 169.2 kg of 1-(2-propenyl)-1,3-dihydro-benzimidazol-2H-one, 780 kg of isopropanol, 2000 kg of water and 220 kg of aqueous Sodium Hydroxide 45% are added. The reaction mixture is heated to 75-85° C. and 160 kg of concentrated hydrochloric acid and 200 kg of water are added. The reaction mixture is stirred at constant temperature for about 45 minutes. After distillation of a mixture of water and Isopropanol (about 3000 kg) the remaining residue is cooled to about 65-75° C. and the pH is adjusted to 6.5-7.5 by addition of 125 kg of aqueous Sodium Hydroxide 45%. After cooling to a temperature of 45-50° C., the pH value is adjusted to 8-9 by addition of about 4 kg of aqueous Sodium Hydroxide 45%. Subsequently the mixture is cooled to 30-35° C. and centrifuged. The residue thus obtained is washed with 340 l of water and 126 l of isopropanol and then with water until chlorides elimination. The wet product is dried under vacuum at a temperature of about 45-55° C. which leads to 358 kg of crude flibanserin polymorph A. The crude product thus obtained is loaded in a reactor with 1750 kg of Acetone and the resulting mixture is heated under stirring until reflux. The obtained solution is filtered and the filtrate is concentrated by distillation. The temperature is maintained for about 1 hour 0-5° C., then the precipitate solid is isolated by filtration and dried at 55° C. for at least 12 hours.

The final yield is 280 kg of pure flibanserin polymorph A.

As mentioned hereinbefore flibanserin polymorph A was characterised by DSC (Differential Scanning Calorimetry). The peak temperature (endothermic maximum) determined for polymorph A is about 161° C. For the characterization via DSC a Mettler TA 3000 System equipped with TC 10-A processor and DSC 20 cell was applied. The heating rate was 10 K/min.

The flibanserin polymorph A was additionally characterised by powder x-ray diffractometry. The x-ray powder diffraction pattern for polymorph A was obtained according to the following conditions:

| Equipment: | Philips PW 1800/10 diffractometer equipped with a digital microvax 2000. | |
|---|---|---|
| Setting parameters: | X-ray | |
| | Type tube: | Cu (long fine focus) |
| | Wavelengths (λ): | $K_{\alpha 1}$ = 1.54060 Å |
| | | $K_{\alpha 2}$ = 1.54439 Å |
| | Intensity ratio ($\alpha 2/\alpha 1$): | 0.500 |
| | Start angle [°2Θ]: | 2.000 |
| | End angle [°2Θ]: | 60.000 |
| | Step size [°2Θ]: | 0.020 |
| | Maximum intensity[s]: | 7310.250 |
| | Type of scan: | continuous |
| | Minimum peak tip width: | 0.00 |
| | Maximum peak tip width: | 1.00 |
| | Peak base width: | 2.00 |
| | Minimum significance: | 0.75 |
| | Number of peaks: | 69 |
| Generator: | high voltage: | 50 KV |
| | tube current: | 30 mA |

The x-ray powder diffraction pattern obtained for polymorph A is illustrated in FIG. 1. The appropriate values are shown below in Table 1.

TABLE 1

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 5.195 | 16.9967 | 17.0390 | 0.960 | 8 | 69 | 0.1 | 1.05 |
| 9.045 | 9.7689 | 9.7931 | 0.100 | 92 | 96 | 1.3 | 0.97 |
| 9.335 | 9.4660 | 9.4896 | 0.080 | 114 | 98 | 1.6 | 0.88 |
| 10.025 | 8.8160 | 8.8379 | 0.140 | 400 | 100 | 5.5 | 7.18 |
| 10.595 | 8.3430 | 8.3637 | 0.140 | 204 | 102 | 2.8 | 3.46 |
| 11.290 | 7.8309 | 7.8503 | 0.140 | 467 | 104 | 6.4 | 6.91 |
| 13.225 | 6.6891 | 6.7058 | 0.180 | 548 | 112 | 7.5 | 13.10 |
| 14.595 | 6.0642 | 6.0793 | 0.180 | 404 | 121 | 5.5 | 9.17 |
| 15.460 | 5.7268 | 5.7410 | 0.140 | 4186 | 125 | 57.3 | 23.20 |
| 16.655 | 5.3185 | 5.3317 | 0.200 | 515 | 130 | 7.0 | 12.38 |
| 17.085 | 5.1856 | 5.1985 | 0.100 | 1347 | 132 | 18.4 | 2.78 |
| 17.285 | 5.1260 | 5.1388 | 0.060 | 1399 | 135 | 19.1 | 2.26 |
| 17.420 | 5.0866 | 5.0992 | 0.100 | 1204 | 135 | 16.5 | 4.71 |
| 18.140 | 4.8863 | 4.8984 | 0.180 | 1043 | 139 | 14.3 | 13.14 |
| 18.650 | 4.7538 | 4.7656 | 0.120 | 1063 | 142 | 14.5 | 0.91 |
| 19.140 | 4.6332 | 4.6447 | 0.140 | 7310 | 144 | 100.0 | 32.77 |
| 19.820 | 4.4757 | 4.4869 | 0.160 | 3624 | 146 | 49.6 | 9.02 |
| 20.080 | 4.4184 | 4.4294 | 0.140 | 5402 | 149 | 73.9 | 21.06 |
| 20.385 | 4.3530 | 4.3638 | 0.160 | 2652 | 149 | 36.3 | 23.25 |
| 21.215 | 4.1845 | 4.1949 | 0.160 | 369 | 154 | 5.0 | 5.78 |
| 21.890 | 4.0570 | 4.0670 | 0.200 | 773 | 156 | 10.6 | 3.09 |
| 22.630 | 3.9259 | 3.9357 | 0.280 | 4277 | 161 | 58.5 | 74.66 |
| 23.210 | 3.8291 | 3.8386 | 0.120 | 484 | 164 | 6.6 | 3.33 |
| 24.355 | 3.6516 | 3.6607 | 0.060 | 2725 | 169 | 37.3 | 1.16 |
| 24.610 | 3.6144 | 3.6234 | 0.140 | 3540 | 172 | 48.4 | 17.08 |
| 24.995 | 3.5596 | 3.5684 | 0.100 | 529 | 174 | 7.2 | 1.01 |
| 25.260 | 3.5228 | 3.5316 | 0.120 | 557 | 174 | 7.6 | 3.02 |
| 26.575 | 3.3514 | 3.3597 | 0.240 | 2421 | 182 | 33.1 | 42.58 |
| 27.155 | 3.2811 | 3.2893 | 0.140 | 676 | 185 | 9.2 | 1.32 |
| 27.310 | 3.2629 | 3.2710 | 0.100 | 767 | 185 | 10.5 | 2.75 |
| 27.865 | 3.1991 | 3.2071 | 0.120 | 420 | 188 | 5.7 | 1.08 |
| 28.210 | 3.1608 | 3.1686 | 0.100 | 1467 | 190 | 20.1 | 0.79 |
| 28.325 | 3.1482 | 3.1560 | 0.140 | 1789 | 190 | 24.5 | 4.41 |
| 28.650 | 3.1132 | 3.1210 | 0.180 | 1204 | 190 | 16.5 | 11.65 |
| 29.520 | 3.0234 | 3.0309 | 0.220 | 1011 | 196 | 13.8 | 15.74 |
| 30.250 | 2.9521 | 2.9594 | 0.120 | 159 | 199 | 2.2 | 1.22 |
| 31.105 | 2.8729 | 2.8800 | 0.360 | 282 | 204 | 3.9 | 8.14 |
| 31.905 | 2.8026 | 2.8096 | 0.100 | 339 | 207 | 4.6 | 0.96 |

TABLE 1-continued

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 32.350 | 2.7651 | 2.7720 | 0.120 | 237 | 210 | 3.2 | 3.01 |
| 33.300 | 2.6884 | 2.6950 | 0.180 | 1347 | 216 | 18.4 | 14.06 |
| 33.640 | 2.6620 | 2.6686 | 0.100 | 404 | 216 | 5.5 | 1.45 |
| 34.880 | 2.5701 | 2.5765 | 0.200 | 202 | 222 | 2.8 | 1.04 |
| 35.275 | 2.5422 | 2.5486 | 0.240 | 299 | 225 | 4.1 | 4.84 |
| 36.055 | 2.4890 | 2.4952 | 0.280 | 202 | 228 | 2.8 | 3.78 |
| 36.910 | 2.4333 | 2.4393 | 0.320 | 169 | 234 | 2.3 | 0.90 |
| 37.160 | 2.4175 | 2.4235 | 0.120 | 216 | 234 | 3.0 | 2.14 |
| 37.680 | 2.3853 | 2.3912 | 0.240 | 240 | 237 | 3.3 | 1.58 |
| 39.435 | 2.2831 | 2.2888 | 0.280 | 449 | 246 | 6.1 | 2.67 |
| 39.675 | 2.2698 | 2.2755 | 0.080 | 396 | 246 | 5.4 | 0.82 |
| 40.325 | 2.2347 | 2.2403 | 0.160 | 520 | 250 | 7.1 | 0.95 |
| 40.930 | 2.2031 | 2.2086 | 0.120 | 480 | 253 | 6.6 | 2.66 |
| 41.445 | 2.1769 | 2.1823 | 0.240 | 372 | 256 | 5.1 | 2.65 |
| 41.990 | 2.1499 | 2.1552 | 0.120 | 538 | 259 | 7.4 | 1.31 |
| 42.670 | 2.1172 | 2.1225 | 0.160 | 428 | 262 | 5.9 | 1.45 |
| 43.145 | 2.0950 | 2.1002 | 0.120 | 433 | 266 | 5.9 | 1.50 |
| 44.190 | 2.0478 | 2.0529 | 0.160 | 376 | 269 | 5.1 | 0.89 |
| 46.095 | 1.9675 | 1.9724 | 0.160 | 279 | 279 | 3.8 | 0.86 |
| 46.510 | 1.9509 | 1.9558 | 0.240 | 310 | 282 | 4.2 | 0.87 |
| 48.305 | 1.8826 | 1.8872 | 0.200 | 506 | 292 | 6.9 | 2.06 |
| 48.900 | 1.8610 | 1.8657 | 0.240 | 615 | 296 | 8.4 | 1.67 |
| 50.330 | 1.8115 | 1.8160 | 0.160 | 437 | 303 | 6.0 | 1.73 |
| 51.035 | 1.7881 | 1.7925 | 0.080 | 416 | 306 | 5.7 | 0.93 |
| 53.550 | 1.7099 | 1.7141 | 0.480 | 177 | 317 | 2.4 | 2.84 |
| 54.500 | 1.6823 | 1.6865 | 0.400 | 130 | 324 | 1.8 | 1.37 |
| 55.420 | 1.6565 | 1.6606 | 0.320 | 130 | 328 | 1.8 | 1.72 |
| 56.220 | 1.6348 | 1.6389 | 0.320 | 121 | 331 | 1.7 | 0.87 |
| 56.770 | 1.6203 | 1.6243 | 0.240 | 142 | 335 | 1.9 | 1.59 |
| 57.405 | 1.6039 | 1.6079 | 0.240 | 112 | 339 | 1.5 | 1.19 |
| 58.500 | 1.5764 | 1.5804 | 0.240 | 67 | 342 | 0.9 | 1.57 |

In the light of the pharmaceutical efficacy of flibanserin, the present invention furthermore relates to the use of flibanserin polymorph A as a medicament.

A further aspect of the present invention relates to the use of flibanserin polymorph A for preparing a pharmaceutical composition for treating diseases in which the use of compounds displaying affinity for the 5-HT$_{1A}$ and 5-HT$_2$-receptor may have a therapeutic benefit.

A further aspect of the present invention relates to the use of flibanserin polymorph A for preparing a pharmaceutical composition for treating a disease selected from depression, schizophrenia, Parkinson, anxiety, sleep disturbances, sexual and mental disorders and age associated memory impairment.

In particular, the instant invention relates to the use of flibanserin polymorph A for the preparation of a medicament for the treatment of disorders of sexual desire.

In a preferred embodiment the invention relates to the use of flibanserin polymorph A for the preparation of a medicament for the treatment of disorders selected from the group consisting of Hypoactive Sexual Desire Disorder, loss of sexual desire, lack of sexual desire, decreased sexual desire, inhibited sexual desire, loss of libido, libido disturbance, and frigidity.

Particular preferred according to the invention is the use of flibanserin polymorph A for the preparation of a medicament for the treatment of disorders selected from the group consisting of Hypoactive Sexual Desire Disorder, loss of sexual desire, lack of sexual desire, decreased sexual desire, inhibited sexual desire.

In a particularly preferred embodiment the invention relates to the use of flibanserin polymorph A for the preparation of a medicament for the treatment of disorders selected from the group of Hypoactive Sexual Desire Disorder and loss of sexual desire.

The aforementioned therapeutic effects of flibanserin polymorph A can be achieved in men and women. However, according to a further aspect of the invention the use of flibanserin polymorph A for the preparation of a medicament for the treatment of female sexual dysfunction is preferred.

The beneficial effects of flibanserin polymorph A can be observed regardless of whether the disturbance existed lifelong or was acquired, and independent of etiologic origin (organic—both, physically and drug induced-, psychogen, a combination of organic—both, physically and drug induced-, and psychogen, or unknown).

As a further feature of the present invention there are provided pharmaceutical compositions comprising as an active ingredient flibanserin polymorph A in addition with one or more pharmaceutical carrier, diluents or excipients. For pharmaceutical administration flibanserin polymorph A may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic glicerides of fatty acids, benzalconium chloride, sodium phosphate, EDTA, polysorbate 80. The compositions are advantageously formulated in dosage units, each dosage unit being adapted to supply a single dose of the active ingredient. Each dosage unit may conveniently contain from 0.01 mg to 100 mg, preferably from 0.1 to 50 mg.

We claim:

1. A crystalline polymorph, designated form A, of flibanserin 1,

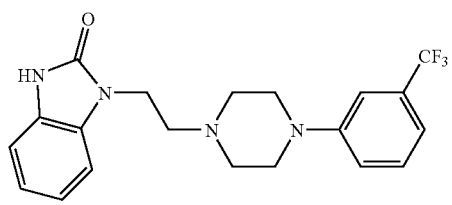

1 having an endothermic maximum at about 161° C. which occurs during thermal analysis using DSC.

2. A polymorph, designated form A, of flibanserin 1, characterized by the following X-ray powder diffraction pattern:

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 5.195 | 16.9967 | 17.0390 | 0.960 | 8 | 69 | 0.1 | 1.05 |
| 9.045 | 9.7689 | 9.7931 | 0.100 | 92 | 96 | 1.3 | 0.97 |
| 9.335 | 9.4660 | 9.4896 | 0.080 | 114 | 98 | 1.6 | 0.88 |
| 10.025 | 8.8160 | 8.8379 | 0.140 | 400 | 100 | 5.5 | 7.18 |
| 10.595 | 8.3430 | 8.3637 | 0.140 | 204 | 102 | 2.8 | 3.46 |
| 11.290 | 7.8309 | 7.8503 | 0.140 | 467 | 104 | 6.4 | 6.91 |

-continued

| Angle [°2Θ] | d-value α1 [Å] | d-value α2 [Å] | Peak width [°2Θ] | Peak int [counts] | Back. int [counts] | Rel. int [%] | Signif. |
|---|---|---|---|---|---|---|---|
| 13.225 | 6.6891 | 6.7058 | 0.180 | 548 | 112 | 7.5 | 13.10 |
| 14.595 | 6.0642 | 6.0793 | 0.180 | 404 | 121 | 5.5 | 9.17 |
| 15.460 | 5.7268 | 5.7410 | 0.140 | 4186 | 125 | 57.3 | 23.20 |
| 16.655 | 5.3185 | 5.3317 | 0.200 | 515 | 130 | 7.0 | 12.38 |
| 17.085 | 5.1856 | 5.1985 | 0.100 | 1347 | 132 | 18.4 | 2.78 |
| 17.285 | 5.1260 | 5.1388 | 0.060 | 1399 | 135 | 19.1 | 2.26 |
| 17.420 | 5.0866 | 5.0992 | 0.100 | 1204 | 135 | 16.5 | 4.71 |
| 18.140 | 4.8863 | 4.8984 | 0.180 | 1043 | 139 | 14.3 | 13.14 |
| 18.650 | 4.7538 | 4.7656 | 0.120 | 1063 | 142 | 14.5 | 0.91 |
| 19.140 | 4.6332 | 4.6447 | 0.140 | 7310 | 144 | 100.0 | 32.77 |
| 19.820 | 4.4757 | 4.4869 | 0.160 | 3624 | 146 | 49.6 | 9.02 |
| 20.080 | 4.4184 | 4.4294 | 0.140 | 5402 | 149 | 73.9 | 21.06 |
| 20.385 | 4.3530 | 4.3638 | 0.160 | 2652 | 149 | 36.3 | 23.25 |
| 21.215 | 4.1845 | 4.1949 | 0.160 | 369 | 154 | 5.0 | 5.78 |
| 21.890 | 4.0570 | 4.0670 | 0.200 | 773 | 156 | 10.6 | 3.09 |
| 22.630 | 3.9259 | 3.9357 | 0.280 | 4277 | 161 | 58.5 | 74.66 |
| 23.210 | 3.8291 | 3.8386 | 0.120 | 484 | 164 | 6.6 | 3.33 |
| 24.355 | 3.6516 | 3.6607 | 0.060 | 2725 | 169 | 37.3 | 1.16 |
| 24.610 | 3.6144 | 3.6234 | 0.140 | 3540 | 172 | 48.4 | 17.08 |
| 24.995 | 3.5596 | 3.5684 | 0.100 | 529 | 174 | 7.2 | 1.01 |
| 25.260 | 3.5228 | 3.5316 | 0.120 | 557 | 174 | 7.6 | 3.02 |
| 26.575 | 3.3514 | 3.3597 | 0.240 | 2421 | 182 | 33.1 | 42.58 |
| 27.155 | 3.2811 | 3.2893 | 0.140 | 676 | 185 | 9.2 | 1.32 |
| 27.310 | 3.2629 | 3.2710 | 0.100 | 767 | 185 | 10.5 | 2.75 |
| 27.865 | 3.1991 | 3.2071 | 0.120 | 420 | 188 | 5.7 | 1.08 |
| 28.210 | 3.1608 | 3.1686 | 0.100 | 1467 | 190 | 20.1 | 0.79 |
| 28.325 | 3.1482 | 3.1560 | 0.140 | 1789 | 190 | 24.5 | 4.41 |
| 28.650 | 3.1132 | 3.1210 | 0.180 | 1204 | 190 | 16.5 | 11.65 |
| 29.520 | 3.0234 | 3.0309 | 0.220 | 1011 | 196 | 13.8 | 15.74 |
| 30.250 | 2.9521 | 2.9594 | 0.120 | 159 | 199 | 2.2 | 1.22 |
| 31.105 | 2.8729 | 2.8800 | 0.360 | 282 | 204 | 3.9 | 8.14 |
| 31.905 | 2.8026 | 2.8096 | 0.100 | 339 | 207 | 4.6 | 0.96 |
| 32.350 | 2.7651 | 2.7720 | 0.120 | 237 | 210 | 3.2 | 3.01 |
| 33.300 | 2.6884 | 2.6950 | 0.180 | 1347 | 216 | 18.4 | 14.06 |
| 33.640 | 2.6620 | 2.6686 | 0.100 | 404 | 216 | 5.5 | 1.45 |
| 34.880 | 2.5701 | 2.5765 | 0.200 | 202 | 222 | 2.8 | 1.04 |
| 35.275 | 2.5422 | 2.5486 | 0.240 | 299 | 225 | 4.1 | 4.84 |
| 36.055 | 2.4890 | 2.4952 | 0.280 | 202 | 228 | 2.8 | 3.78 |
| 36.910 | 2.4333 | 2.4393 | 0.320 | 169 | 234 | 2.3 | 0.90 |
| 37.160 | 2.4175 | 2.4235 | 0.120 | 216 | 234 | 3.0 | 2.14 |
| 37.680 | 2.3853 | 2.3912 | 0.240 | 240 | 237 | 3.3 | 1.58 |
| 39.435 | 2.2831 | 2.2888 | 0.280 | 449 | 246 | 6.1 | 2.67 |
| 39.675 | 2.2698 | 2.2755 | 0.080 | 396 | 246 | 5.4 | 0.82 |
| 40.325 | 2.2347 | 2.2403 | 0.160 | 520 | 250 | 7.1 | 0.95 |
| 40.930 | 2.2031 | 2.2086 | 0.120 | 480 | 253 | 6.6 | 2.66 |
| 41.445 | 2.1769 | 2.1823 | 0.240 | 372 | 256 | 5.1 | 2.65 |
| 41.990 | 2.1499 | 2.1552 | 0.120 | 538 | 259 | 7.4 | 1.31 |
| 42.670 | 2.1172 | 2.1225 | 0.160 | 428 | 262 | 5.9 | 1.45 |
| 43.145 | 2.0950 | 2.1002 | 0.120 | 433 | 266 | 5.9 | 1.50 |
| 44.190 | 2.0478 | 2.0529 | 0.160 | 376 | 269 | 5.1 | 0.89 |
| 46.095 | 1.9675 | 1.9724 | 0.160 | 279 | 279 | 3.8 | 0.86 |
| 46.510 | 1.9509 | 1.9558 | 0.240 | 310 | 282 | 4.2 | 0.87 |
| 48.305 | 1.8826 | 1.8872 | 0.200 | 506 | 292 | 6.9 | 2.06 |
| 48.900 | 1.8610 | 1.8657 | 0.240 | 615 | 296 | 8.4 | 1.67 |
| 50.330 | 1.8115 | 1.8160 | 0.160 | 437 | 303 | 6.0 | 1.73 |
| 51.035 | 1.7881 | 1.7925 | 0.080 | 416 | 306 | 5.7 | 0.93 |
| 53.550 | 1.7099 | 1.7141 | 0.480 | 177 | 317 | 2.4 | 2.84 |
| 54.500 | 1.6823 | 1.6865 | 0.400 | 130 | 324 | 1.8 | 1.37 |
| 55.420 | 1.6565 | 1.6606 | 0.320 | 130 | 328 | 1.8 | 1.72 |
| 56.220 | 1.6348 | 1.6389 | 0.320 | 121 | 331 | 1.7 | 0.87 |
| 56.770 | 1.6203 | 1.6243 | 0.240 | 142 | 335 | 1.9 | 1.59 |
| 57.405 | 1.6039 | 1.6079 | 0.240 | 112 | 339 | 1.5 | 1.19 |
| 58.500 | 1.5764 | 1.5804 | 0.240 | 67 | 342 | 0.9 | 1.57 |

3. A pharmaceutical composition comprising form A according to claim 1, optionally in admixture with one or more pharmaceutical carriers, diluents or excipients, wherein the polymorph is present in crystalline form.

4. A pharmaceutical composition comprising a polymorph, designated form A, of flibanserin 1 according to claim 2, optionally in admixture with one or more pharmaceutical carriers, diluents or excipients, wherein the polymorph is present in crystalline form.

5. Form A of flibanserin 1

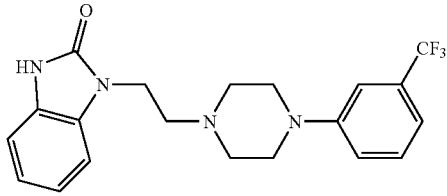

having an endothermic maximum at about 161° C. which occurs during thermal analysis using DSC, and obtained by the process comprising:

(a) reacting a benzimidazolone 2

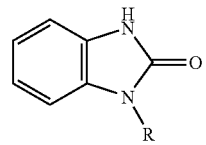

wherein R denotes a suitable amino protecting group, with a piperazine 3

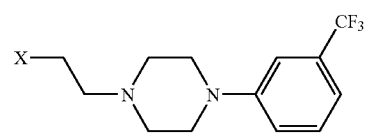

wherein X is a leaving group selected from chlorine, bromine, iodine, methanesulphonate, trifluoromethansulphonate and para-toluenesulphonate, in a suitable solvent selected from water, alcohols, mixtures of water with alcohols, polar aprotic solvents and mixtures of polar aprotic solvents with water, in the presence of a suitable base, and (b) cleaving the amino protecting group R under suitable cleaving conditions.

6. A pharmaceutical composition comprising form A of flibanserin 1

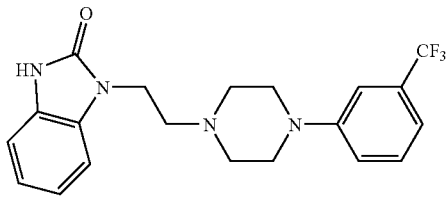

having an endothermic maximum at about 161° C. which occurs during thermal analysis using DSC, and obtained by the process-comprising:

(a) reacting a benzimidazolone 2

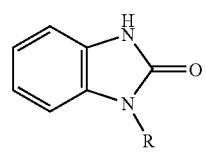

wherein R denotes a suitable amino protecting group, with a piperazine 3

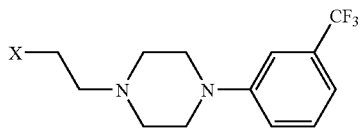

wherein X is a leaving group selected from chlorine, bromine, iodine, methanesulphonate, trifluoromethansulphonate and para-toluenesulphonate, in a suitable solvent selected from water, alcohols, mixtures of water with alcohols, polar aprotic solvents and mixtures of polar aprotic solvents with water, in the presence of a suitable base, and (b) cleaving the amino protecting group R under suitable cleaving conditions.

7. A polymorph, designated form A, of flibanserin 1,

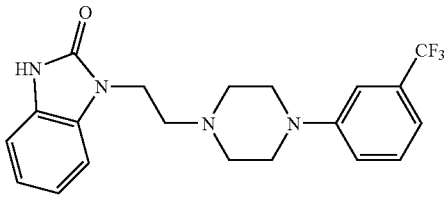

having an endothermic maximum at about 161° C. which occurs during thermal analysis using DSC, and characterized by an X-ray powder diffraction pattern comprising peaks (°2Θ) at 15.460, 19.140, 19.820, 20.080, 22.630, 24.610, 24.355, 26.575, 28.210 and 28.325.

8. A polymorph, designated form A, of flibanserin 1,

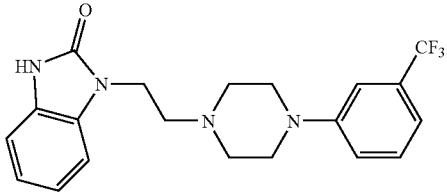

characterized by a powder X-ray diffraction patent comprising peaks (°2Θ) at 15.460, 19.140, 19.820, 20.080, 22.630, 24.610, 24.355, 26.575, 28.210 and 28.325.

9. A polymorph, designated form A, of flibanserin 1,

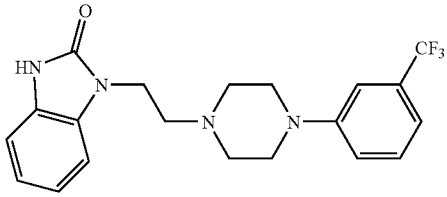

having an endothermic maximum at about 161° C. which occurs during thermal analysis using DSC, and characterized by an X-ray powder diffraction pattern comprising peaks (°2Θ) at 5.195, 9.045, 9.335, 10.025, 10.595, 11.290, 13.225, 14.595, 15.460, 16.655, 17.085, 17.285, 17.420, 18.140, 18.650, 19.140, 19.820, 20.080, 20.385, 21.215, 21.890, 22.630, 23.210, 24.355, 24.610, 25.995, 25.260, 26.575, 27.155, 27.310, 27.865, 28.210, 28.325, 28.650, 29.520, 30.250, 31.105, 31.905, 32.350, 33.300, 33.640, 34.880, 35.275, 36.055, 36.910, 37.160, 37.680 39.435, 39.675, 40.325, 40.930, 41.445, 41.990, 42.670, 43.145, 44.190, 46.095, 46.510, 48.305, 48.900, 50.330, 51.035, 53.550, 54.500, 55.420, 56.220, 56.770, 57.405, and 58.500.

10. A polymorph, designated form A, of flibanserin 1,

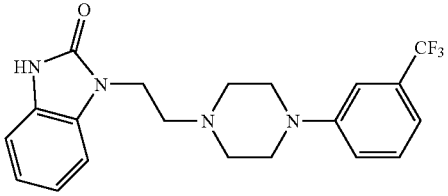

characterized by an X-ray powder diffraction pattern comprising peaks (°2Θ) at 5.195, 9.045, 9.335, 10.025, 10.595, 11.290, 13.225, 14.595, 15.460, 16.655, 17.085, 17.285, 17.420, 18.140, 18.650, 19.140, 19.820, 20.080, 20.385, 21.215, 21.890, 22.630, 23.210, 24.355, 24.610, 25.995, 25.260, 26.575, 27.155, 27.310, 27.865, 28.210, 28.325, 28.650, 29.520, 30.250, 31.105, 31.905, 32.350, 33.300, 33.640, 34.880, 35.275, 36.055, 36.910, 37.160, 37.680 39.435, 39.675, 40.325, 40.930, 41.445, 41.990, 42.670, 43.145, 44.190, 46.095, 46.510, 48.305, 48.900, 50.330, 51.035, 53.550, 54.500, 55.420, 56.220, 56.770, 57.405, and 58.500.

11. A pharmaceutical composition comprising a polymorph designated form A, of flibanserin 1 according to claim 7, optionally in admixture with one or more pharmaceutical carriers, diluents or excipients, wherein the polymorph is present in crystalline form.

12. A pharmaceutical composition comprising a polymorph, designated form A, of flibanserin 1 according to claim 8, optionally in admixture with one or more pharmaceutical carriers, diluents or excipients, wherein the polymorph is present in crystalline form.

13. A pharmaceutical composition comprising a polymorph, designated form A, of flibanserin 1 according to claim 9, optionally in admixture with one or more pharmaceutical carriers, diluents or excipients, wherein the polymorph is present in crystalline form.

14. A pharmaceutical composition comprising a polymorph, designated form A, of flibanserin 1 according to claim 10, optionally in admixture with one or more pharmaceutical carriers, diluents or excipients, wherein the polymorph is present in crystalline form.

15. A polymorph, designated form A, of flibanserin 1 characterized by having an X-ray powder diffraction pattern as shown in FIG. 1.

16. A pharmaceutical composition comprising a polymorph, designated form A, of flibanserin 1 according to claim 15, optionally in admixture with one or more pharmaceutical carriers, diluents or excipients, wherein the polymorph is present in crystalline form.

* * * * *

UNITED STATES PATENT AND TRADEMARK OFFICE
CERTIFICATE OF CORRECTION

PATENT NO.       : 7,420,057 B2                                Page 1 of 1
APPLICATION NO.  : 11/546304
DATED            : September 2, 2008
INVENTOR(S)      : Bombarda et al.

It is certified that error appears in the above-identified patent and that said Letters Patent is hereby corrected as shown below:

In Column 11, claim 8, line 46, and claim 9, line 62, each occurrence of the term "(°20Θ)" should be changed to --(°2Θ)--

Signed and Sealed this

Thirtieth Day of December, 2008

JON W. DUDAS
*Director of the United States Patent and Trademark Office*